United States Patent [19]
Howard et al.

[11] Patent Number: 5,779,694
[45] Date of Patent: Jul. 14, 1998

[54] MAGNETIC STEREOTACTIC SYSTEM FOR TREATMENT DELIVERY

[75] Inventors: Matthew A. Howard; Marc Mayberg; M. Sean Grady, all of Seattle, Wash.; Rogers C. Ritter; George T. Gillies, both of Charlottesville, Va.

[73] Assignee: The University of Virginia Alumni Patents Foundation, Charlottesville, Va.

[21] Appl. No.: 96,214

[22] Filed: Jul. 19, 1993

Related U.S. Application Data

[60] Continuation of Ser. No. 904,032, Jun. 25, 1992, abandoned, which is a division of Ser. No. 463,340, Jan. 10, 1990, Pat. No. 5,125,888.

[51] Int. Cl.$^6$ .................... A61M 37/00; A61M 1/00; A61K 9/22
[52] U.S. Cl. .................. 604/891.1; 604/95; 604/158; 604/174; 600/12; 600/13
[58] Field of Search ................ 604/890.1, 891.1, 604/93, 95, 158, 174; 600/12, 13

[56] References Cited

U.S. PATENT DOCUMENTS

| | | |
|---|---|---|
| 2,589,349 | 3/1952 | Drefenbach . |
| 2,863,458 | 12/1958 | Modny et al. .................... 600/12 X |
| 3,043,309 | 7/1962 | McCarthy .................... 600/12 X |
| 3,358,676 | 12/1967 | Frei et al. . |
| 3,474,777 | 10/1969 | Figge . |

(List continued on next page.)

FOREIGN PATENT DOCUMENTS

| | | |
|---|---|---|
| 281869 | 10/1913 | Germany . |
| 1284528 | 12/1968 | Germany . |
| 2450098 | 4/1976 | Germany . |
| 2929429 | 2/1980 | Germany . |
| 0002383 | 7/1982 | Japan . |

OTHER PUBLICATIONS

Stauffer et al., "Observations of the Use of Ferromagnetiz Implants for Inducing Hyperthermia", *IEEE Transactions of Biomedical Engineering* (USA 1984).

Thackray et al., "Indirect Heating Source for Treatment of Malignant Brain Tumors", *Electrocomponent Science & Technology*, pp. 91–96 (USA 1974).

Oldendorf, "Speculations on the Instrumentation of the Nervous System", Proceedings of San Diego Symposium for Biomedical Eng., 2:274–280 (U.S.A 1962).

Senyei et al., "Magnetic Guidance of Drug–Carrying Microspheres", J. Appl. Phys. 49(6):3578–3582 (U.S.A. 1978).

*Primary Examiner*—Mary Beth Jones
*Attorney, Agent, or Firm*—James Creighton Wray; Meera P. Narasimhan

[57] ABSTRACT

A treatment delivery apparatus comprises a metallic object and a treatment carrier device which is connected by a heat-sensitive biodegradable connector link to the magnetic object. This carrier device contains the treatment, i.e. the drug, to be transported. An electromagnet is positioned outside of the body part for producing a magnetic field which captures the magnetic object. This electromagnet may be either a simple coil system attached to a robotic arm which moves the electromagnet adjacent the body part, or a multicoil electromagnet system surrounding the body part. In either case, the robotically moved electromagnet or multicoil electromagnet system moves the magnetic object within the body part to a desired location. A computer controls either the robotic arm or multicoil current magnitudes and directions. This computer also provides visualization for observing the location and movement of the magnetic object and carrier device. Upon reaching the desired location, the magnetic object is heated, which causes the heat-sensitive biodegradable connector link to melt, which separates the drug-containing carrier device from the magnetic object. The electromagnet means then moves the magnetic object back out of the body part. The treatment-containing carrier device remains in the desired location and the drug is delivered to the specific location.

13 Claims, 9 Drawing Sheets

U.S. PATENT DOCUMENTS

| | | |
|---|---|---|
| 3,626,940 | 12/1971 | Zaffaroni . |
| 3,653,385 | 4/1972 | Burton . |
| 3,674,014 | 7/1972 | Tillander . |
| 3,794,041 | 2/1974 | Frei et al. . |
| 3,941,119 | 3/1976 | Corrales ................................ 604/95 X |
| 4,013,063 | 3/1977 | Bucalo . |
| 4,136,683 | 1/1979 | Gordon . |
| 4,186,729 | 2/1980 | Harison . |
| 4,269,826 | 5/1981 | Zimmermann et al. . |
| 4,323,056 | 4/1982 | Borelli et al. . |
| 4,340,038 | 7/1982 | McKean . |
| 4,351,337 | 9/1982 | Sidman . |
| 4,364,377 | 12/1982 | Smith . |
| 4,434,341 | 2/1984 | Busby . |
| 4,445,501 | 5/1984 | Bresler . |
| 4,501,726 | 2/1985 | Schroder et al. . |
| 4,690,130 | 9/1987 | Mirell . |
| 4,869,247 | 9/1989 | Howard, III et al. . |

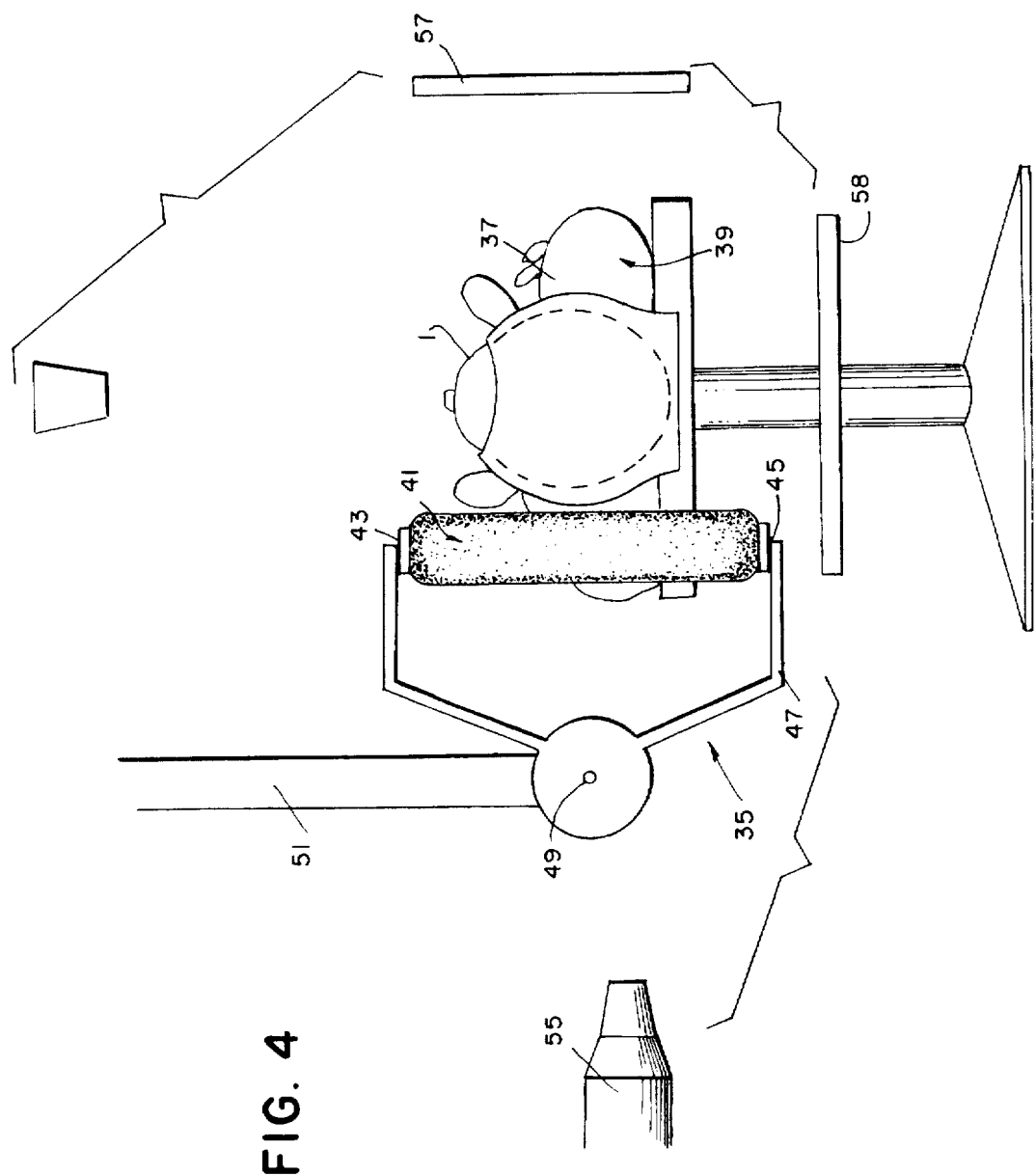

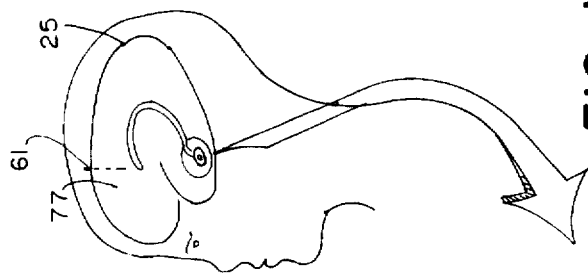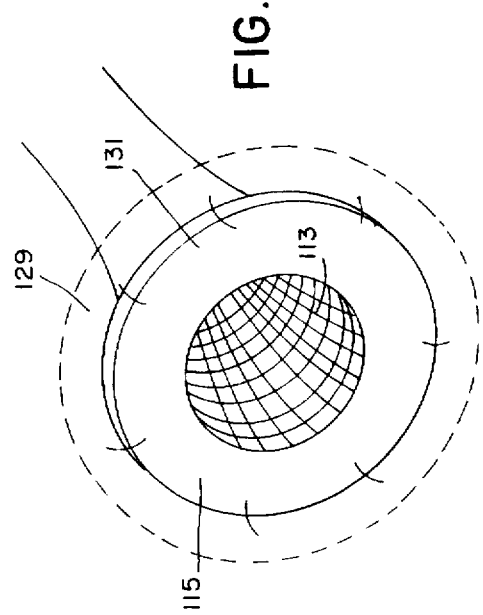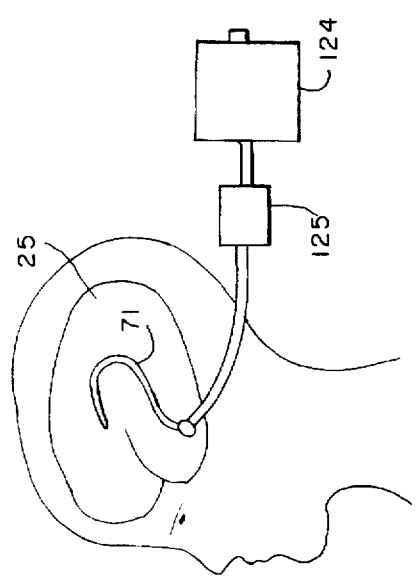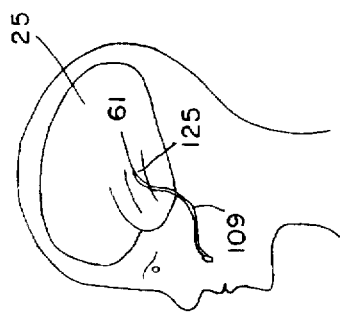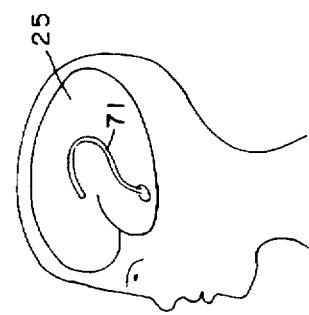

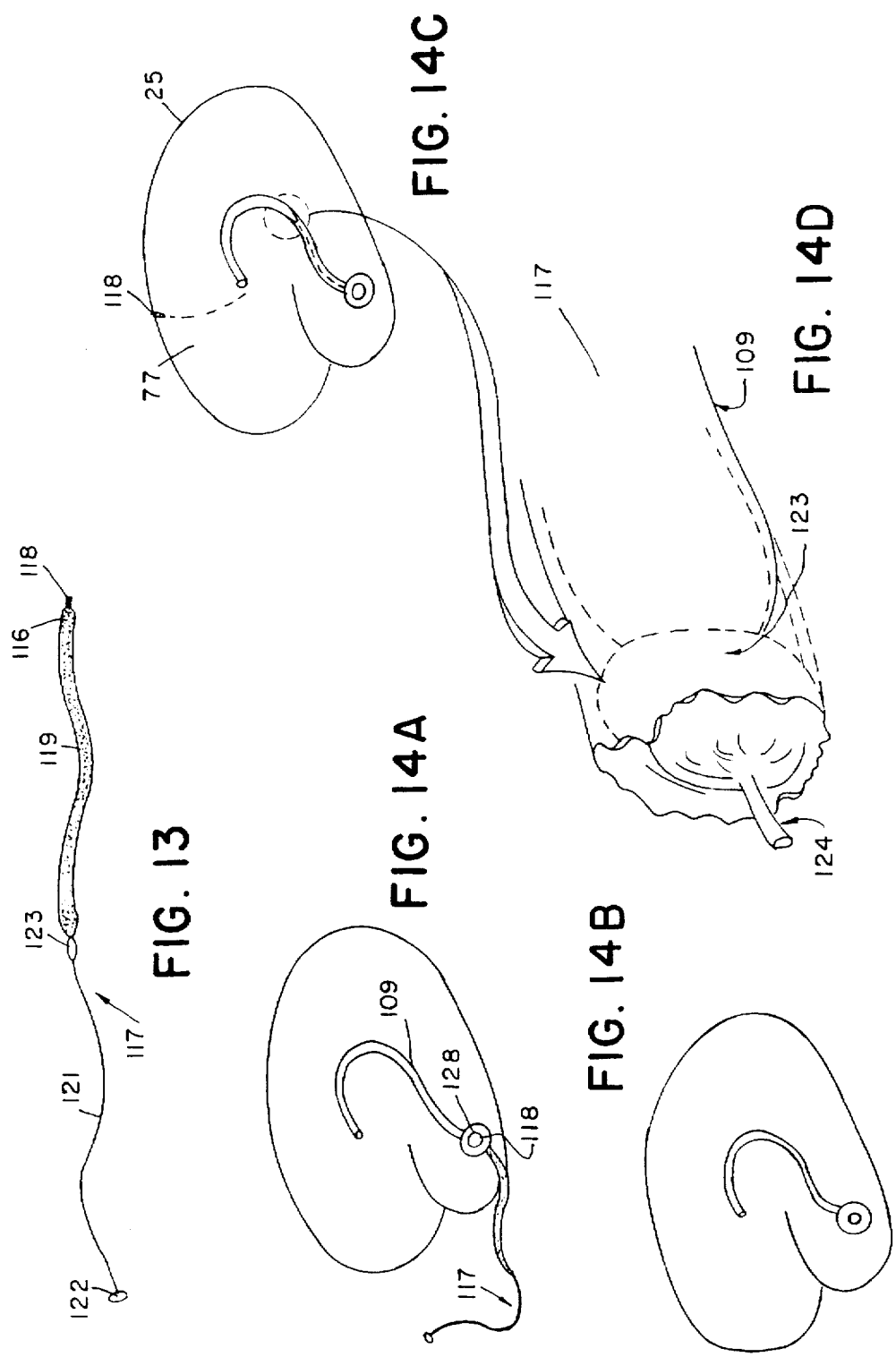

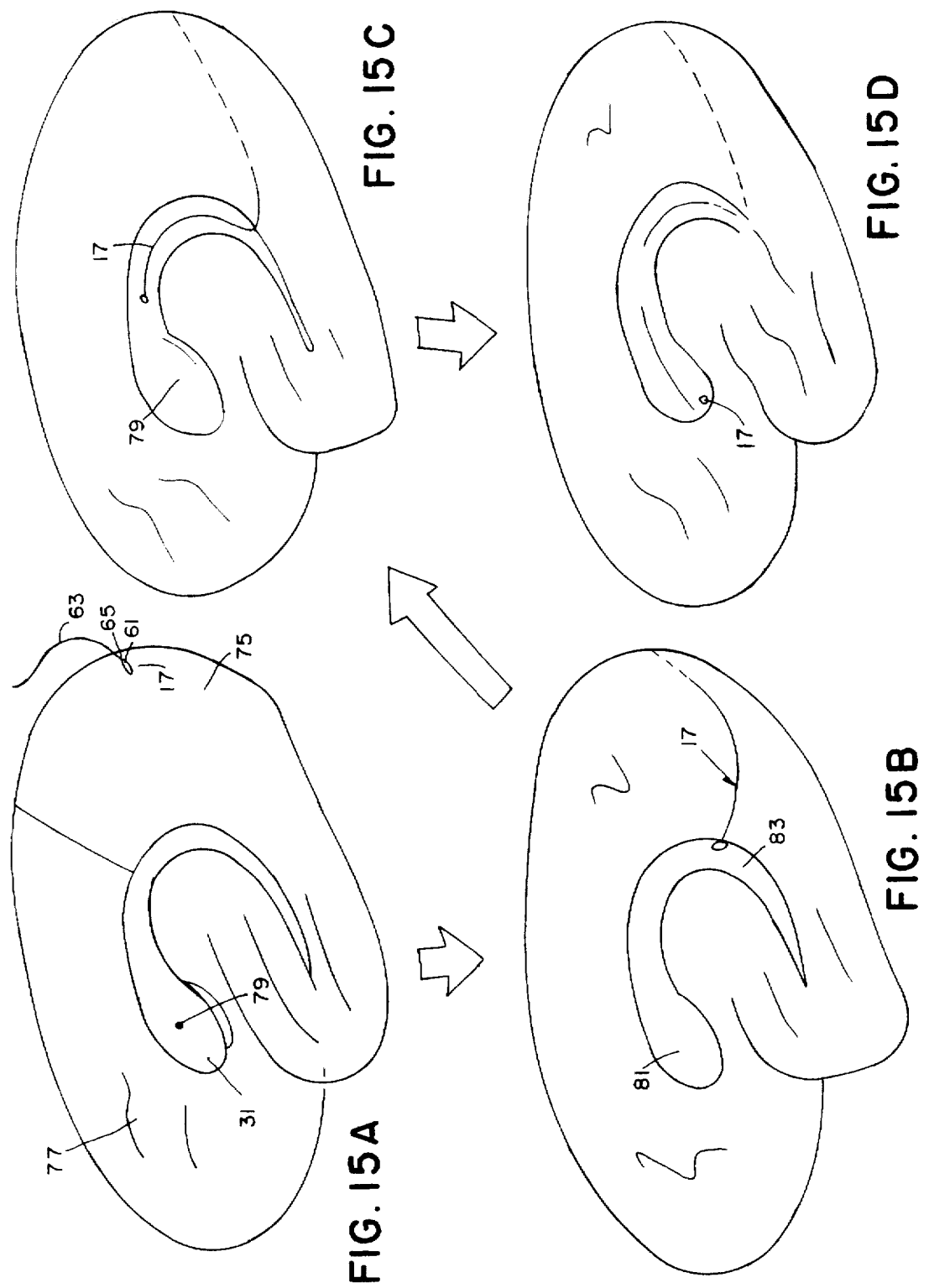

MAGNETIC STEREOTACTIC SYSTEM FOR TREATMENT DELIVERY

This application is a continuation of application Ser. No. 904,032 filed Jun. 25, 1992, now abandoned, which is a division of application Ser. No. 463,340, filed Jan. 10, 1990, now U.S. Pat. No. 5,125,888.

BACKGROUND OF THE INVENTION

1. Field of the Invention

This invention relates to an apparatus for delivering treatment to a specific location in a portion of the body and the method of using this apparatus to achieve this treatment delivery. More specifically, this invention relates to the use of a magnetic object to achieve this treatment delivery to the specific location in the body part.

2. Prior Art

Current treatment delivery techniques used for the treatment of many illnesses, especially neurological disorders, are suboptimal. The major limitations to existing methods result from lack of regional specificity within the body portion being treated. This lack of regional specificity refers to the inability to cause drugs, etc. to localize to specific regions most affected by the disease being treated.

This is especially true of the brain. As an example, in Parkinson's disease dopaminergic innervation of a specific subcortical structure called the striatum is lost. Pharmacologic therapy is intended to restore dopamine function in the striatum, but in practice pharmacologic agents are given systemically, resulting in the entire brain being bathed in these chemicals. It is thought that many of the serious side effects observed with conventional therapy result from unnecessary pharmacologic stimulation of normal brain outside the targeted region (striatum). Another example is temporal lobe epilepsy. In this disorder only one portion of the brain displays abnormal electrical activity, but current treatments involve exposing the entire brain to potentially toxic drugs.

The brain presents an additional major limitation to existing methods due to the inability of the drugs to pass through the blood brain barrier. The blood brain barrier (BBB) refers to the unique permeability properties of the cerebral vasculature. Unlike systemic blood vessels, cerebral vessels are generally quite impermeable, thus the term BBB. Many drugs that pass easily through systemic blood vessels cannot pass through the BBB and enter the brain. This dramatically reduces the ability to deliver the desired drugs to the brain. An example of this is Parkinson's disease. The molecule that is lost in this disorder is dopamine. Ideally the disorder would be treated by delivering dopamine to the brain. However, the BBB is impermeable to dopamine and this agent cannot be used systemically, that is orally or intravenously. Instead, a less optimal strategy has been adopted of providing a BBB permeable precursor to dopamine synthesis, L-DOPA.

The invention described below has been designed to circumvent the shortcomings of conventional therapy and to provide an ideal treatment delivery system for the treatment of diseases, especially focal neurological disorders.

SUMMARY OF THE INVENTION

With this invention, treatment such as with drugs will be chronologically and directly delivered to specific locations in a particular body part by way of a magnetically guided, treatment carrier means.

In one embodiment of the invention, the treatment carrier means is a polymeric implant with a linear, string-like configuration that presents a very small cross-sectional area as it is led through the body by a thin leading magnet. The polymer string is also very flexible so that the trailing string follows precisely the leading magnet as it is directed along the body. This flexibility results in the polymer string sliding along the tunnel created by the leading magnet.

In another embodiment, this treatment carrier means is a flexible gelatin structure or a flexible hollow biodegradable tube which encases the drug or a slurry of cells.

In another embodiment, the treatment carrier means is an implant sheath device with a permeable region which is placed within the specific body location and a nonpermeable region. The distal end of the nonpermeable region remains at the surface of the body. A pump may be attached to the distal end and treatment infused to determine an appropriate dose-response calculation. This treatment may be chronologically pumped, infused or, preferably, a semi-permeable membrane catheter filled with the treatment is magnetically placed inside the implant sheath device.

In the preferred embodiment, the magnetic means has an approximately 2 mm cross-sectional diameter and has a torpedo-like shape.

The treatment carrier means is attached to the magnetic object by a connection means so that, when the treatment carrier means is located in the specific location, the magnetic object and treatment carrier means may be separated. This connection means could consist of a heat-soluble biodegradable connector link so that the magnetic object could be inductively heated and cause the melting of this heat-soluble biodegradable connector link. This connection means could also be a spring-mechanical mechanism so that the magnetic object is disconnected from the treatment carrier means by a simple magnetic pulse sequence. Other types of connection means are also envisioned for connecting and later separating the magnetic object from the treatment carrier means.

This apparatus and method are especially useful to chronically and directly deliver drugs or a slurry of cells to precise regions of the brain. The flexibility of the treatment carrier means allows it to follow precisely the leading magnet as it is directed along the uneven contours of the brain target region. This flexibility results in the treatment carrier means sliding along the tunnel created by the magnetic object and assuming a final position and a shape that precisely follows the convoluted volume of the brain target.

The preferred magnetic guidance system is found in U.S. application Ser. No. 167,217 entitled "HGR Video Tumor Fighter", and this apparatus and method are incorporated herein. The ability to precisely manipulate a small intracranial magnetic object has already been demonstrated using the HGR Video Tumor Fighter system. Basically, an electromagnet is positioned outside of the body part for producing a magnetic field which captures the magnetic object. This electromagnet may be either a simple coil system attached to a robotic arm which moves the electromagnet adjacent the body part, or a multicoil, superconducting electromagnet system surrounding the body part. In either case, the robotically moved electromagnet or multicoil electromagnet system moves the magnetic object within the body part to a desired location. A computer controls either the robotic arm or the multicoil current magnitudes and directions. The computer also provides visualization for observing the location and movement of the magnetic object and treatment carrier means.

The advantages of this invention with treatment delivery to precise regions of the brain are as follows:

1. The BBB is bypassed. By delivering drugs or cells directly into brain tissue, access is gained to the targeted tissue without having to pass through a blood vessel and across the BBB.
2. Drugs or cells are delivered to the specific targeted subregion of the brain. As the drugs are released from the polymer, they diffuse to immediately adjacent brain regions but do not unnecessarily expose the remainder of the brain.
3. Drugs are released chronically in a controlled release fashion. Polymeric compounds can be designed to release the drug over a period of many months or several years.
4. Optimal dispersion of polymer is achieved by remote, non-linear magnetic manipulation. Most brain structures that will be desired treatment delivery targets have non-linear contours. As an example, one element of the striatum is arranged in the shape of a "C". Given a fixed volume of polymer, the ideal dispersion configuration would maximize the ratio of:

(target volume within diffusion distance of polymer)/(degree of mechanical displacement of target volume by polymer implant).

A thin string of polymer contoured exactly to the non-linear configuration of the subcortical target structure maximizes this ratio. Remote manipulation is the only means by which to safely achieve this final configuration.

5. The procedure will be safe, simple and quick. Experience to date with the HGR Video Tumor Fighter supports the contention that the procedure can be performed under local anesthetic with a very low complication rate. Precision magnetic movements with accurate brain imaging techniques can be achieved.
6. This treatment delivery technique can be used to treat a wide variety of neurologic disorders. Examples include neurodegenerative disorders (e.g. Parkinson's disease, Alzheimer's disease) where neurotransmitter replacement therapy would be administered, and focal epilepsy where antiepileptic drugs or inhibitory neurotransmitters would be delivered to the sites of the seizure focus.

Other advantages and features of the invention will be apparent from the disclosure, which includes the above and ongoing specification with the claims and the drawings.

BRIEF DESCRIPTION OF THE DRAWINGS

FIG. 4 shows an embodiment of the magnetic drive and fluoroscopic imaging components of the magnetic stereotactic system with a patient in position.

FIG. 5A shows a right lateral view of this system; FIG. 5B shows an overhead view of this system;

FIG. 5C shows a rear view of this system; and FIG. 5D shows a frontal view of this system.

FIGS. 12A–D illustrate the embodiment of the invention shown in FIG. 11 being magnetically directed into the striatum of the brain. Specifically, FIG. 12A shows the leading magnet placed on the brain surface; FIG. 12B shows the magnetic carrier complex being magnetically directed into the striatum of the brain; FIG. 12C illustrates the release of the leading magnet and it being magnetically directed out of the brain; and FIG. 12D illustrates how the temporal lobe end of the sheath of the present invention is secured to the dura by way of the flange.

FIG. 13 illustrates the membrane implant coupled to a leading magnet by a connecting means.

FIGS. 14A–D illustrate the placement of the membrane implant shown in FIG. 13 being magnetically directed into the flexible treatment carrier means shown in FIG. 9. Specifically, FIG. 14A shows the leading magnet placed into sheath lumen; FIG. 14B shows the magnetic carrier complex being directed into the sheath; FIG. 14C illustrates that the leading magnet has been disconnected and directed out of the frontal lobe of the brain; and FIG. 14D shows a partial enlargement of the membrane implant within the implant sheath device.

FIGS. 15A–D illustrate another embodiment of the magnetic carrier being magnetically directed into the striatum of the brain. Specifically, FIG. 15A shows the leading magnet placed on the brain surface; FIG. 15B shows the magnetic carrier complex being directed into the tail of the caudate nucleus in the striatum of the brain; FIG. 15C shows the magnetic carrier complex advancing within the volume of the caudate nucleus; and FIG. 15D illustrates the magnetic carrier in its final position within the caudate nucleus in the striatum of the brain.

FIG. 16 shows a reservoir and pump means supplying directly to the area which requires necessary treatment.

DETAILED DESCRIPTION OF THE DRAWINGS

Figure 1A:
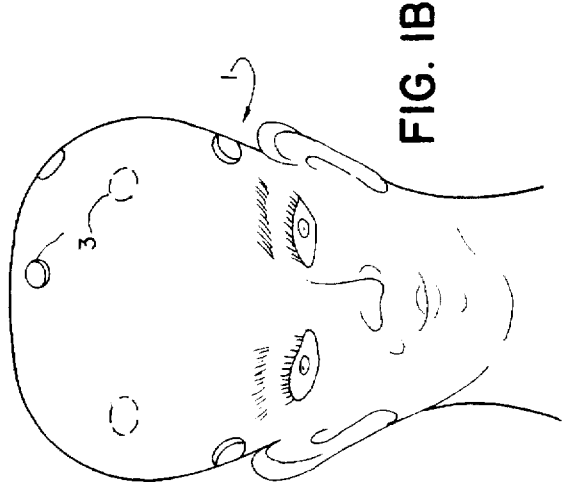
FIGS. 1A and 1B show diagrams of the skull fiducial marker system.
Figure 1B:
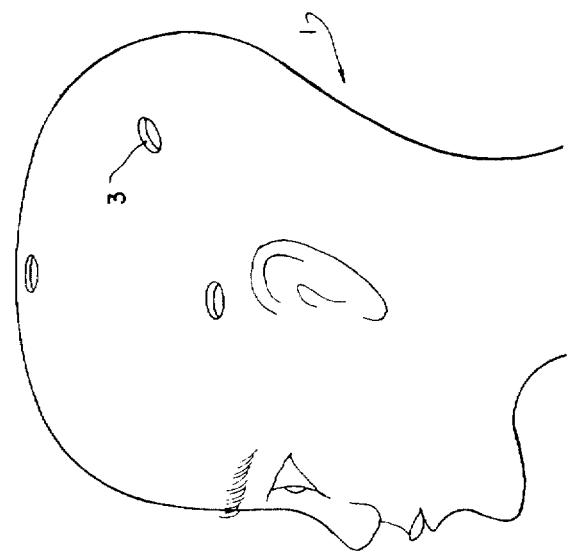

Referring to the drawings, FIGS. 1A–B diagram the skull fiducial marker system. A patient's head 1 is shown with fiducial skull markers 3 (radiopaques). In this instance, five markers are depicted.

Figure 2A:
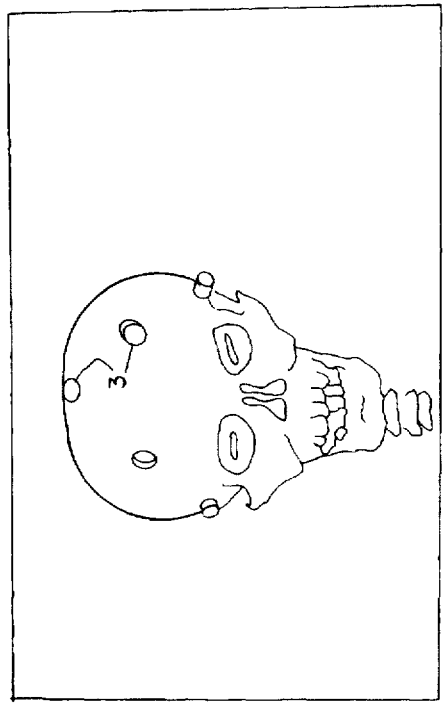
FIGS. 2A and 2B illustrate the fluoroscopic images (AP+LAT) from the skull fiducial marker system.
Figure 2B:
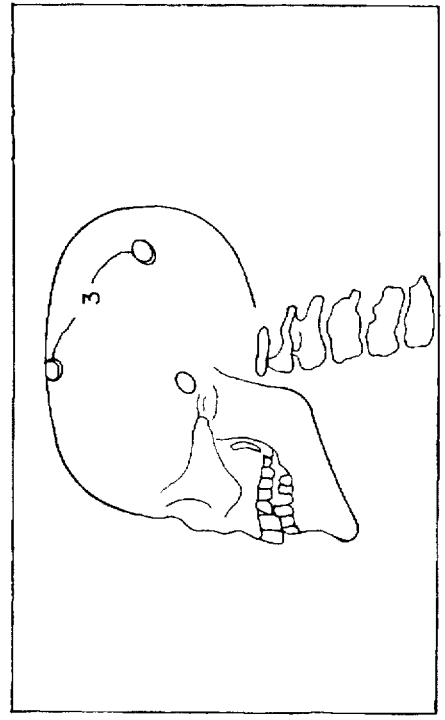

FIGS. 2A–B show fluoroscopic images (AP+LAT) from the skull fiducial marker system.

Figure 3:
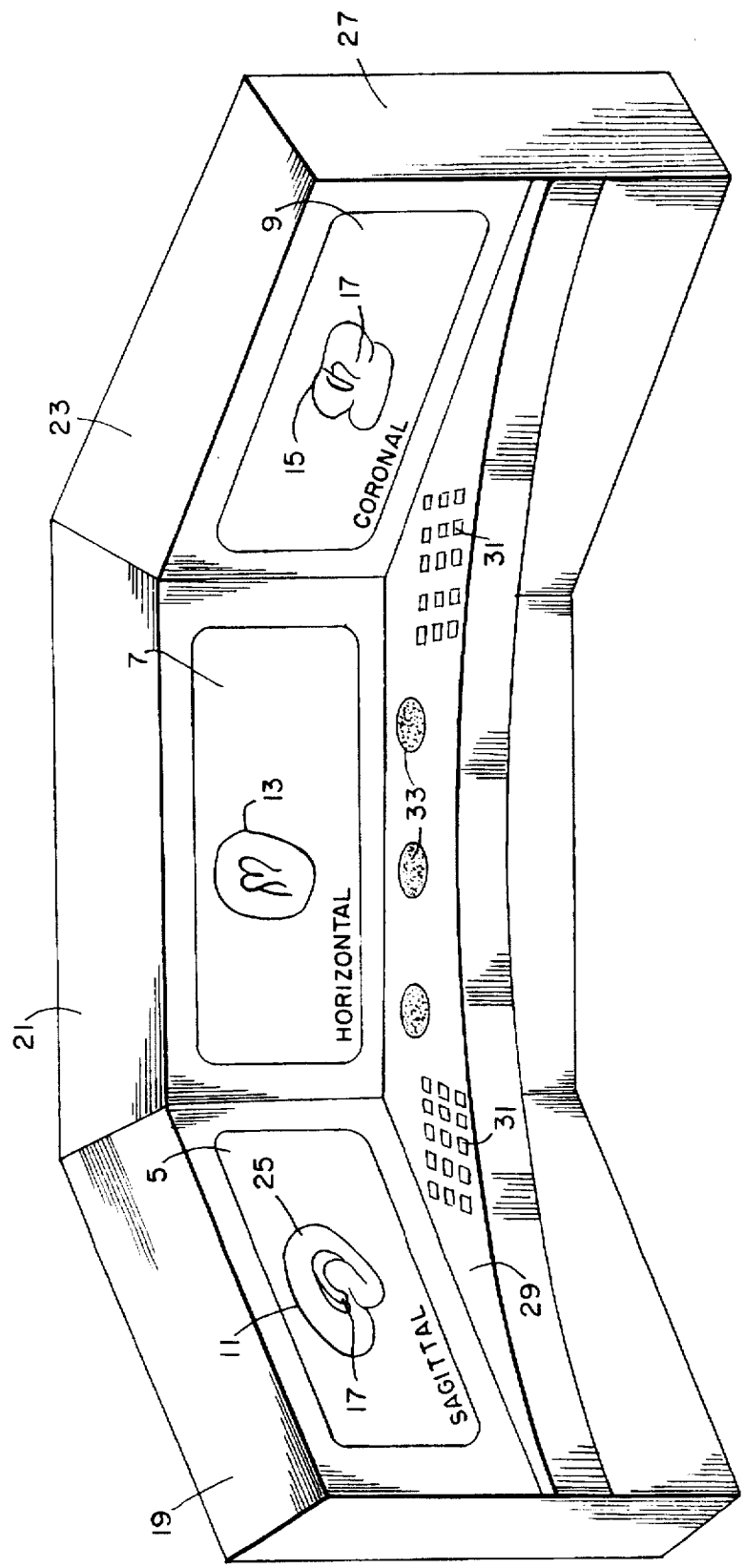
FIG. 3 illustrates a frontal view of an embodiment of the magnetic stereotactic system computer control terminal.

FIG. 3 shows an embodiment of the magnetic stereotactic system computer control terminal. The surgeon (not shown) faces three screens 5, 7, 9 of displays 19, 21, 23, showing CT scan images 11, 13, 15 of the brain 25 and the location of the magnetic carrier 17. CT scan image 11 is a sagittal view of the brain 25. CT scan image 13 is a horizontal view of the brain. CT scan image 15 is a coronal view of the brain.

The computer console 29 of computer 27, as controlled by terminals 31 and guided controls 33 operated by a surgeon (not shown), steers the magnetic carrier 17 through the brain to the desired location.

The computer 27 is used to record physiological data of the brain from MRI and/or CT scans and angiograms, and is used to store and reproduce the data to form the images 11, 13, 15 of the brain 25 on the screens 5, 7, 9, and is used to correlate the real time imaging of the magnetic carrier 17 with the previous recorded data and to currently display the images.

FIG. 4 illustrates one embodiment of a magnetic drive 35 and the fluoroscopic imaging components of the magnetic stereotactic system with patient 37 in position. The patient's head 1 is held in place by an immobilizing head holder 39.

The magnetic drive components 35 consist of a superconducting drive magnet 41, which is pivotally connected at its ends 43, 45 to a holder 47. Holder 47 is pivotally connected at 49 to a robot control arm 51. This allows the drive magnet 41 to be robotically positioned to direct the magnetic carrier.

The fluoroscope imaging component consists of automated biplanar fluoroscopes 53, 55, and fluoroscreens 57 and 58. The fluoroscopes 53, 55 are perpendicularly oriented.

FIGS. 5A–D show a second embodiment of the magnetic drive comprising a multicoil, superconducting electromagnet system 87 which surrounds the body part. With this embodiment, changing the current in the multicoil, superconducting electromagnets direct the magnetic carrier within the body part to a desired location.

Figure 5B:
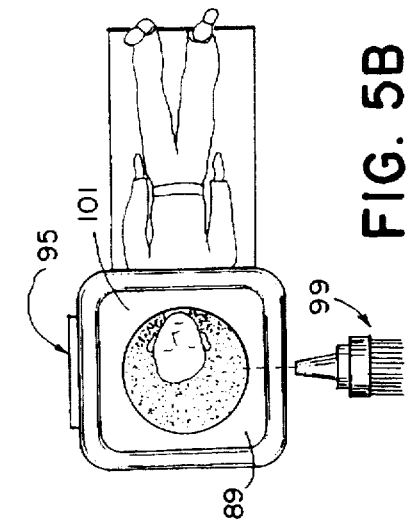
FIGS. 5A-D illustrate another embodiment of a magnetic drive system of the present invention using superconducting drive magnets. Specifically.
Figure 5D:
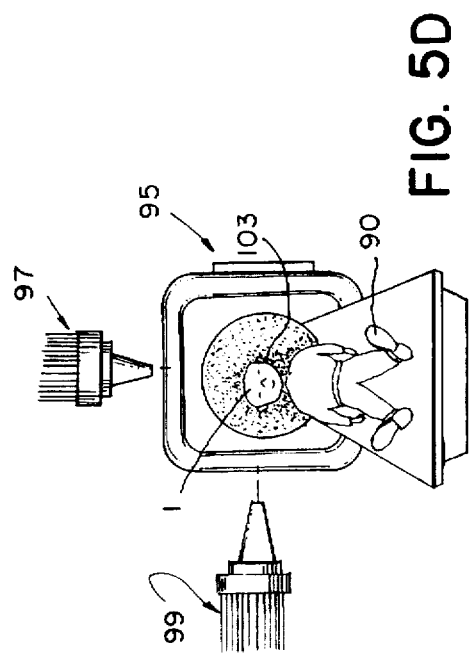
Figure 5A:
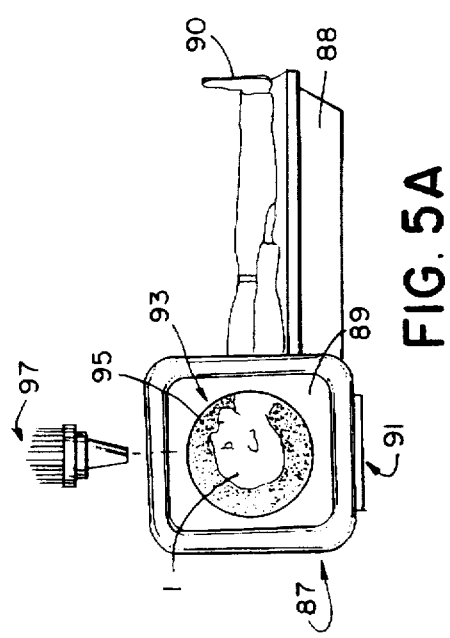

FIG. 5A shows the right lateral view of the multicoil, superconducting electromagnet system 87 comprising a cryostat 89 which houses the multicoil, superconducting electromagnets (not shown). Attached to cryostat 89 is an inferior X-ray detector 91 and a left lateral X-ray detector 95. The inferior X-ray detector 91 and left lateral X-ray detector 95 are phosphorous screens. The cryostat 89 has a side port 93 which allows X-rays from the right lateral X-ray emitter (not shown) to pass through. The left lateral X-ray detector 95 processes the X-rays from the right lateral X-ray emitter. The multicoil, superconducting electromagnet system 87 also includes an overhead X-ray emitter 97. The inferior X-ray detector 91 processes the X-rays from the overhead X-ray emitter 97. FIG. 5A further shows platform 88 on which the patient 90 lays while the multicoil superconducting electromagnetic system is being used about the patient's head 1.

FIG. 5B shows an overhead view of the multicoil, superconducting electromagnetic system, which includes the right lateral X-ray emitter 99. This view also shows that attached to the cryostat is the left lateral X-ray detector 95. The cryostat 89 is also shown with the overhead port 101, which allows X-rays from the overhead emitter to pass through the cryostat.

Figure 5C:
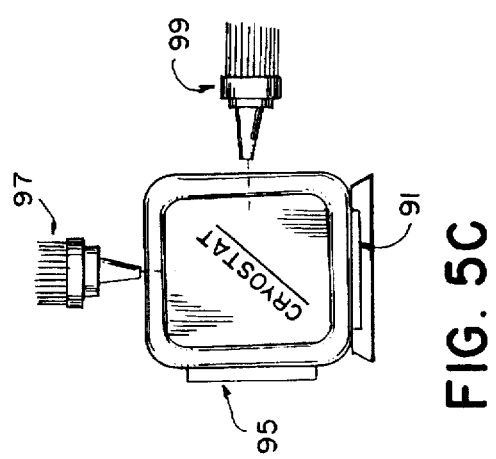

FIG. 5C shows a rear view of the multicoil, superconducting electromagnetic system, which shows that the inferior X-ray detector, which is attached to the bottom of the cryostat, is opposite the overhead X-ray emitter 97 and left lateral X-ray detector 95, which is opposite the right lateral X-ray emitter 99.

FIG. 5D illustrates a frontal view of the multicoil, superconducting electromagnetic system, which shows the overhead X-ray emitter 97, the right lateral X-ray emitter 99, and the left lateral X-ray detector 95. This figure also shows the opening 103 in the cryostat in which the head 1 of the patient 90 passes through, so that only the head is exposed to the X-rays.

Figure 6:
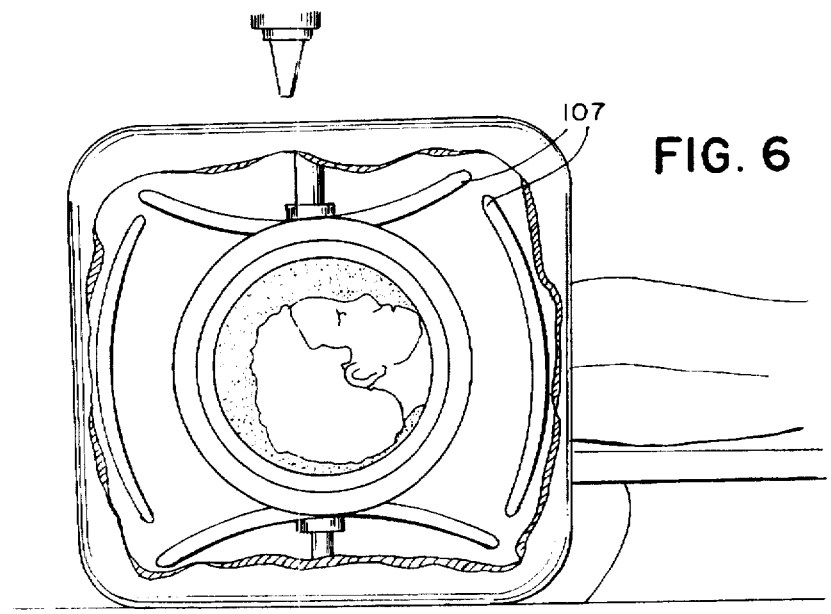
FIG. 6 shows a lateral view of the embodiment of the magnetic drive system of FIG. 5 with the walls cut-away to show the superconducting drive magnets.

FIG. 6 shows a lateral view of the cryostat 89 with the cryostat wall cut-away to expose the superconducting electromagnetic coils 107.

Figure 7:
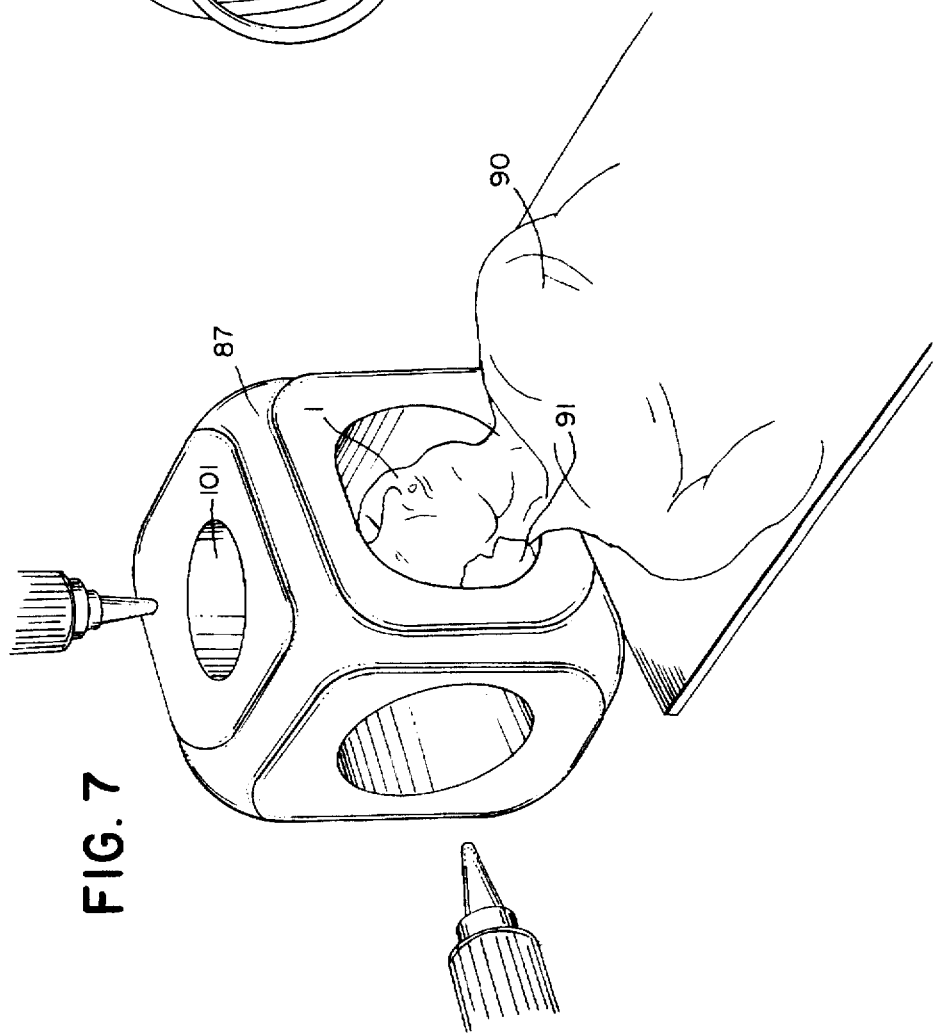
FIG. 7 illustrates an off-axis view of a patient's head in the embodiment of the magnetic drive system of FIGS. 5A–D.

FIG. 7 shows an off-axis view of patient 90 in the cryostat 87. As can be seen in this figure, the patient's head 1 rests on the inferior X-ray detector 91 and faces upward towards overhead port 101.

Figure 8:
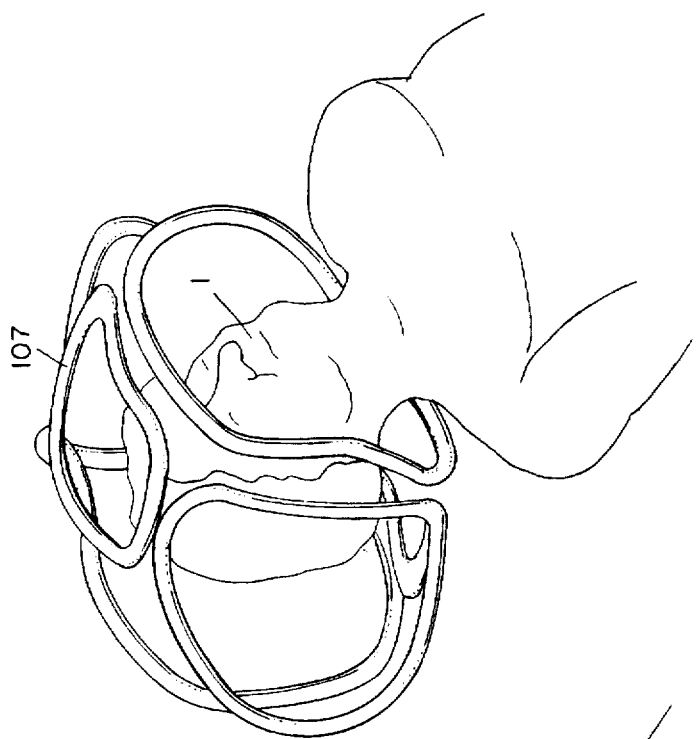
FIG. 8 illustrates another off-axis view of the superconducting coils positioned around the patient's head without the cryostat being depicted.

FIG. 8 shows an off-axis view of the superconducting coils 107 positioned about the patient's head 1. The cryostat has been removed in order to show the structure of the superconducting electromagnetic coils 107.

Figure 9:
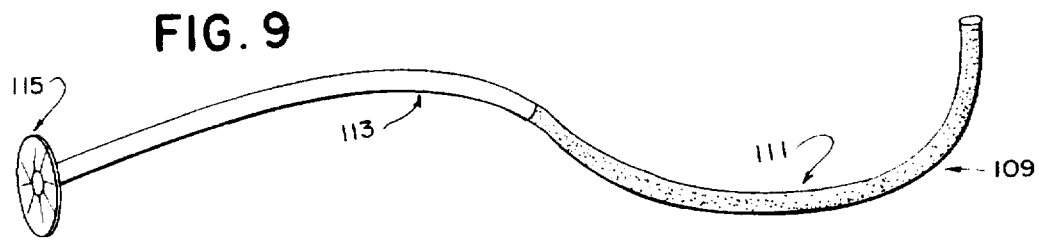
FIG. 9 shows one embodiment of a flexible treatment carrier means.
Figure 10:
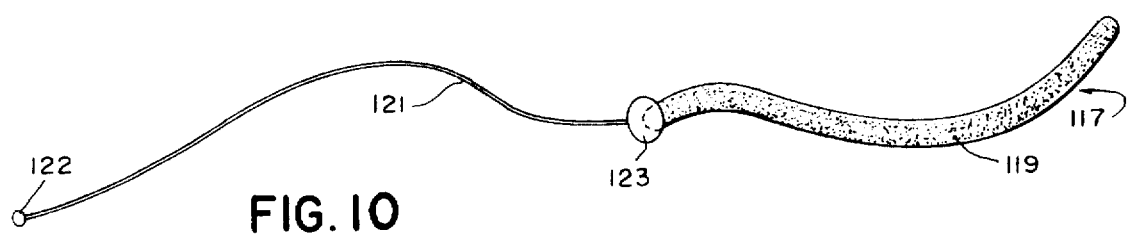
FIG. 10 illustrates an embodiment of a membrane implant which can be inserted into the carrier means shown in FIG. 9.

FIG. 9 shows an embodiment of the flexible treatment carrier means. This embodiment is an implant sheath device 109 which has a permeable region 111 and a non-permeable region 113. The permeable region ill allows all macromolecules to pass through the sheath device, but does not allow cells to pass. The nonpermeable region 113 serves simply as a transport tube. A flange device 115 is sewn to the distal end of the non-permeable region 113 of the implant sheath device 109. This flange device allows the transport tube to be capped. The implant sheath device bends easily without kinking, and the sheath wall is very resistant to compressing or collapsing forces. The sheath remains wide open, even when empty and surrounded by the body part. The internal surface of the implant sheath device is very smooth, allowing easy passage of a membrane implant (FIG. 10). The sheath wall is less than about 0.3 mm thick, and the outer diameter of the sheath is approximately 3.0 mm. When this implant sheath device is to be used within the striatum of the brain, the length of the permeable region 111 and non-permeable region 113 are approximately 8 cm in length.

FIG. 10 illustrates an embodiment of the membrane implant 117 which can be inserted into the implant sheath device. The membrane implant 117 has semi-permeable region 119 and a retrieval tail 121, which attaches to a cuff 123. The cuff 123 is attached at the distal end of the semi-permeable region 119. The semi-permeable region 119 is flexible, will not rupture and will not stick within the implant sheath device. In one embodiment of the membrane implant, the membrane has a cross-sectional diameter of approximately 2 mm. As shown in this figure, cuff 123 is inflated. When inflated, the cuff 123 prevents diffusion of substances into the non-permeable region of the implant sheath device. The retrieval tail 121 has attached to its distal end an infusion port 122. The retrieval tail 121 is hollow so that air placed into the infusion port 122 enters the retrieval tail 121 to inflate cuff 123. When the membrane implant is used for transporting treatment to the striatum of the brain, preferably the semi-permeable membrane region and retrieval tail 121 are approximately 8 cm in length.

Figure 11:
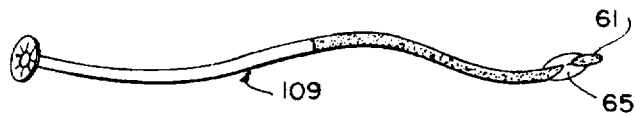
FIG. 11 shows one embodiment of the present invention, using the flexible treatment carrier means shown in FIG. 9.

FIG. 11 shows the implant sleeve device 109 connected to the leading magnet 61 by connecting means 65. In this figure, the connecting means is a heat-sensitive polymer.

FIGS. 12A–D illustrate the placement of the implant sleeve device into the striatum of the brain.

FIG. 12A shows the implant sleeve device 109 connected to the leading magnet 61. This magnetic-coupled implant sheath is placed on the surface of the middle temporal gyrus 125 of brain 25.

FIG. 12B shows the sheath after it has been magnetically directed into the striatum 71 of the brain 25.

FIG. 12C shows the leading magnet after it has been released with RF heating pulse and has been magnetically directed out of the frontal lobe 77 of brain 25.

FIG. 12D shows the attachment of flange device 115 to the distal end of the non-permeable region 113 which allows flange device 115 and the implant sleeve device to be sewn to the dura 129 by sutures 131.

FIG. 13 shows the membrane implant 117, which comprises the semi-permeable membrane 119, a cuff 123, a retrieval tail 121 and infusion port 122, coupled to the leading magnet 61 by connecting means 65. In this embodiment of the membrane implant, the connecting means is a heat-sensitive polymer. Also in FIG. 13, the cuff 123 is deflated.

FIGS. 14A–D show the placement of the membrane implant 117 into the implant sleeve device 109.

FIG. 14A shows the leading magnet 61 is placed into the sheath lumen 128.

FIG. 14B shows that the membrane implant has been magnetically directed fully within the sheath.

FIG. 14C shows that the leading magnet 61 has been disconnected and has been magnetically directed out of frontal lobe 77 of brain 25.

FIG. 14D shows an enlargement of the membrane implant 117 within the implant sheath device 109. As shown in FIG. 14D, the cuff 123 is inflated, the infusion port (not shown) is filled with air which inflates the cuff through the infusion lumen 124 which connects to the cuff 123. The inflated cuff prevents seeping of chemicals into the nonpermeable region of the implant sheath device.

FIGS. 15A–D graphically depict another embodiment of the magnetic carrier being magnetically directed into the striatum 71 of brain 25. The magnetic carrier 17 consists of a leading magnet 61 and a flexible treatment carrier means, which is shown in FIGS. 15A–D as being a string polymer 63. This carrier means is connected to the leading magnet by a connecting means 65.

FIG. 15A shows the magnetic carrier 17 placed on the brain surface 73 near the occipital lobe 75 of brain 25. Also shown in FIG. 15A is caudate nucleus 79 of caudate 81 found in the striatum 71 of brain 25. Also shown is frontal lobe 77 of brain 25.

FIG. 15B shows the magnetic carrier 17 entering the tail 83 of the caudate 81.

FIG. 15C illustrates the magnetic carrier 17 being advanced within the volume of the caudate nucleus 79.

In FIG. 15D, the magnetic carrier 17 is shown in its final position.

FIG. 16 shows a reservoir 124 and pump means 125 supplying directly to the area which requires necessary treatment.

The following is an example of how this system works and some variations on the design of the apparatus used in this method. Although this example describes using this method in the brain, this method is easily adapted for use with other body parts.

Radiopaque fiducial markers are placed into the patient's skull, as with a standard HGR Video Tumor Fighter operation. These markers serve as a reference system by which the magnetic stereotactic system computer correlates fluoroscopic and CT images. Next, a standard CT or MRI scan is obtained and the subcortical target volumes are identified. These data are incorporated and analyzed by computer. Three-dimensional coordinates occupied by vascular structures, tumor, or eloquent areas of brain are recorded. The eloquent areas of brain are identified using a conventional stereotactic atlas and the loci for these structures are programmed into the software. This information is then resynthesized and projected as a video image on one or more screens facing the surgeon.

This image recreates the spatial relationship between the position of the magnetic carrier and the previously mentioned areas of importance in a form that can be understood by the surgeon and enables him to avoid zones of danger and minimize damage as he makes his approach to the region of treatment.

After imaging is complete, an incision is made through the scalp, a burr hole is drilled, dura reflected and the leading magnet is placed on the exposed brain with the polymer string attached. The surgeon takes his position at the controls facing the video screen. The drive magnet is positioned and activated, creating a magnetic gradient which causes the magnetic carrier to move. Direction of movement and real-time localization of the magnetic carrier is achieved using automated biplanar fluoroscopes. The computer rapidly performs triangulation calculations with the fluoroscopic data to locate the magnetic carrier. Magnetic carrier location information is presented to the surgeon as a video image of the preoperative CT or MRI scan with a superimposed image of the magnetic carrier. The large drive magnet positioned outside the patient's head is oriented by a robotic device controlled by the surgeon. Alternatively a multicell magnet with various component currents controlled by the surgeon through a computer representation performs the same function. The computer continuously calculates the magnitude and direction of magnetic field gradient of the drive magnet (using either a measurement of its current or appropriate measurements of the magnetic field) at the location of the magnetic carrier leading magnetic, and presents a representation on the screen(s) of the direction and strength of the force applied to the magnetic carrier's leading magnet.

By adjusting the position and current of the drive magnet, and observing the movement of the magnetic carrier on the video screen(s), the surgeon is able to precisely direct the magnetic carrier through the brain.

As the leading magnet of the magnetic carrier travels through the brain, the flexible polymer string follows behind, sliding through the small tunnel that has been created by the leading magnet. The surgeon directs the leading magnet into one end of the target structure, then travels throughout the convoluted target volume until the polymer string is left draped along the entire structure. At that point the leading magnet is mechanically disconnected from the polymer string. Techniques that may be used to execute this disconnection would include inductively heating the leading magnet to cause melting of a heat-soluble biodegradable connector link, disconnection by a spring-mechanical mechanism triggered by a simple magnetic pulse sequence, or other methods.

After the polymer string has been positioned properly and released, the disconnected leading magnet is carefully directed back to the burr hole and removed. For treatment delivery applications where the potential for adverse side effects due to drug overdose exist, additional safety measures would be included to allow easy retrieval of the polymer. This would include: 1) placing one polymer string initially with the leading magnet left in place for a short period of observation. Should adverse effects be noted, the polymer is then magnetically directed out of the head. 2) Designing a very thin retrieval tail to the polymer implant. This retrieval tail would be biologically inert, and remain anchored to the skull surface after the polymer string has been placed. Should adverse effects be noted the retrieval tail would be used to gently pull the polymer string out of the brain.

In another embodiment, the treatment carrier means will consist of a flexible gelatin structure or a flexible hollow biodegradable tube which encases a slurry of cells, such as fetal cells, which will be carried to the specific location in the body part. Since this carrier means is flexible, the carrier means may be configured to limit the area into which the cells will be released, which will limit the cell growth to that specific location in the body part. This will allow the cells to grow where they are needed in order to produce the necessary treatment, such as producing a needed drug, while avoiding interference with cell growth in other parts of this particular body location. This slurry of cells will consist of fetal neurons or genetically engineered cells. This slurry of cells may also be loaded into a hollow, flexible, biodegradable string.

A further embodiment of this treatment carrier means is a flexible implant sheath device. Again, this flexibility of the treatment carrier means allows the implant sheath device to be configured in a non-linear fashion throughout a specific location in this particular body part. A distal end of this implant sheath device remains at the surface of the body and is attached to a pump system and reservoir. This allows the treatment to be pumped directly to that area which requires this necessary treatment.

Alternatively, a semi-permeable membrane implant that is filled with the drug may be substituted for the pump. This membrane implant will be magnetically placed inside the implant sheath device and will release drugs in a highly controlled manner.

Additionally, in another embodiment of this treatment carrier means, the treatment to be delivered is incorporated into the polymer string itself during the synthetic process.

The method and apparatus incorporates delivery of all forms of treatment, including drugs, proteins and neurotrophic compounds.

While the invention has been described with reference to specific embodiments, modifications and variations of the invention may be constructed without departing from the scope of the invention, which is described in the following claims.

We claim:

1. A drug delivering apparatus comprising:
   a) a magnetic means for inserting in a body part;
   b) a carrier means for carrying a treatment to a specific location in the body part; and
   c) a connection means for releasably connecting the carrier means to the magnetic means and for disengaging the carrier means from the magnetic means.

2. The drug delivering apparatus of claim 1, further comprising:
   d) electromagnet means positioned outside the body part for producing a magnetic field which captures the magnetic means;
   e) positioning means connected to the electromagnet means for moving the electromagnet means adjacent the body part, wherein the electromagnet means moves the magnetic means within the body part to a specific location;
   f) control means connected to the positioning means for controlling the positioning means' movement of the electromagnet means; and
   g) visualization means for observing location and movement of the magnetic means and the carrier means.

3. The drug delivering apparatus of claim 1, further comprising:
   d) electromagnet means positioned outside the body part for producing a magnetic field which captures the magnetic means;
   e) positioning means for changing the current in a multicoil electromagnet wherein the electromagnet means moves the magnetic means within the body part to a specific location;
   f) control means connected to the current changing means for adjusting various currents to the multicoil electromagnet means; and
   g) visualization means for observing location and movement of the magnetic means and the carrier means.

4. The apparatus of claim 1, wherein the magnetic means has an approximately 2 mm cross-sectional diameter.

5. The apparatus of claim 1, wherein the magnetic means has generally a shape like a torpedo.

6. The apparatus of claim 1, wherein the carrier means is a polymer compound.

7. The apparatus of claim 6, wherein the polymer compound is in string form.

8. The apparatus of claim 1, wherein the carrier means is an implant tubular device which comprises a permeable region at a proximal end of the tubular device and a non-permeable region at a distal end of the tubular device, both of which have distal and proximal ends; and a flange device which is attached to the distal end of the non-permeable region, wherein the permeable region is located within the specific location in the body part and the non-permeable region has a sufficient length so that the flange device can be attached to a surface of the body.

9. The apparatus of claim 8, further comprising a pump means for pumping the treatment through the non-permeable region into the permeable region.

10. The apparatus of claim 8, further comprising a membrane implant which can be inserted into the implant tubular device at the flange device into the non-permeable region, the membrane implant having a semi-permeable membrane at a proximal end of the membrane implant, wherein the semi-permeable membrane has a proximal and distal end; a cuff which is attached at the distal end of the semi-permeable membrane; a retrieval tail which has a proximal and distal end, wherein the proximal end is attached to the cuff and the distal end is attached to an infusion port.

11. The apparatus of claim 10, further comprising a second magnetic means for inserting into the implant tubular device and a connection means for connecting the membrane implant to the second magnetic means and for disengaging the membrane implant from the second magnetic means.

12. The apparatus of claim 1, wherein the carrier means is a flexible gelatin structure.

13. The apparatus of claim 1, wherein the connection means is a heat-sensitive biodegradable connector link.

* * * * *